United States Patent [19]

Nissen

[11] Patent Number: 4,883,817

[45] Date of Patent: * Nov. 28, 1989

[54] RAISING CHICKENS FOR MEAT PRODUCTION WITH KETOISOCAPROATE-CONTAINING FEEDS

[75] Inventor: Steven L. Nissen, Ames, Iowa

[73] Assignee: Iowa State University Research Foundation, Inc., Ames, Iowa

[*] Notice: The portion of the term of this patent subsequent to Aug. 16, 2005 has been disclaimed.

[21] Appl. No.: 20,606

[22] Filed: Mar. 2, 1987

[51] Int. Cl.$^4$ ............................................. A61K 31/19
[52] U.S. Cl. ................................................... 514/557
[58] Field of Search ........................................ 514/557

[56] References Cited

U.S. PATENT DOCUMENTS

| 4,100,161 | 7/1978 | Walser | 424/274 |
| 4,100,293 | 7/1978 | Walser | 424/274 |
| 4,677,121 | 6/1987 | Walser et al. | 514/561 |

OTHER PUBLICATIONS

Baker and Boebel, J. An. Sci. (1981), 53:125–129.
Rogers and Harper, J. Nutr. (1965), 87:267–273.
Saiper and Walser, Metabolism (1977), 25:301–308.
Walser (1983), "New Aspects of Clinical Nutrition", pp. 319–324, Nitrogen–Sparing Effects of Branched Chain Ketoacids (Karger, Basel).
Chawla, et al., J. Nutr. (1975), 105:798–803.
Boebel and Baker, J. Nutr. (1982), 112:1929–1939.
Chow and Walser, J. Nutr. (1974), 104:1208–1214.
Walser, Clin. Sci. (1984), 66:1–15.

*Primary Examiner*—Frederick E. Waddell
*Attorney, Agent, or Firm*—Tilton, Fallon, Lungmus & Chestnut

[57] ABSTRACT

Alpha-ketoisocaproate (KIC) is fed to young chickens to increase their rate of weight gain during the growth period from 0 to 6 weeks of age. The KIC may be combined with a complete feed ration for the baby chickens.

10 Claims, No Drawings

RAISING CHICKENS FOR MEAT PRODUCTION WITH KETOISOCAPROATE-CONTAINING FEEDS

FIELD OF INVENTION

The field of this invention is the raising of chickens for meat production with growth promoting feeds. The invention is particularly concerned with the feeding of alpha-ketoisocaproate to chickens.

BACKGROUND OF INVENTION

Keto analogs of essential amino acids have been proposed for use in human nutrition as partial or complete substitutes for the corresponding amino acids, including, for example, leucine, isoleucine, methionine, phenylalanine, and valine. Originally the use of such keto analogs was proposed by Dr. MacKenzie Walser as supplementation to protein-reduced diets in uremia. See, for example, Walser, et al., *J. Clin. Inv.* (1973) 52:678–690. Further experiments by Walser and associates demonstrated a nitrogen sparing effect from mixtures of branchedchain keto acids. Saiper and Walser, *Metabolism* (1977) 26:301–308. Patents have issued to Walser on the use of keto analogs of essential amino acids for promotion of protein synthesis and suppression of urea formation in humans. (U.S. Pat. Nos. 4,100,161 and 4,101,293). A recent review summarized existing knowledge with respect to the administration of branched-chain keto acids to humans. "New Aspects of Clinical Nutrition," pp. 319–324 (Karger, Basel, 1983).

The keto acid analog of L-leucine is alpha-ketoisocaproate (KIC) which is also sometimes referred to as "ketoleucine". KIC does not have L and D forms as does leucine. It is known that there is an interconversion of circulating KIC and leucine. Published studies have demonstrated that KIC can be substituted in animal diets for leucine providing that larger molar amounts of KIC are used.

Chawla et al. reported that weight loss by rats being fed a diet deficient in leucine could be prevented by adding equimolar amounts of KIC to the diet. *J. Nutr.* (1975) 105:798803. Other studies in rats have demonstrated that KIC is utilized less efficiently than leucine. Boebel et al. reported that the efficiency of KIC was only about 56% with reference to leucine. Boebel and Baker, *J. Nutr.* (1982) 112:1929–1939. Chow et al. obtained similar results, reporting that substitution of KIC for leucine reduced feed efficiency by approximately 33%. Chow and Walswer, *J. Nutr.* (1974), 104:1208–1214.

Walser and associates have published a study of the oral dosing of KIC to rats in which an increased efficiency of utilization of nitrogen was apparently observed. Abras and Walser, *Am. J. Clin. Nutr.* (1982) 36:154–161. There are no known reports describing the feeding of KIC to poultry for any purpose.

SUMMARY OF INVENTION

This invention is based on the discovery that the oral administration of alpha-ketoisocaproate (KIC) to young chickens can appreciably increase their rate of weight gain. It was found that their growth promotant effect is related to both the age and diet of the chickens. Favorable results can be obtained by feeding KIC to chickens from 0 to 6 weeks of age. The optimum feeding period appears to be from about 0 to 4 weeks. The chickens are fed a protein-adequate diet with KIC as an additive. Diets appreciably deficient in protein tend to interfere with the growth promotant effect of KIC.

The KIC feeding method of this invention is particularly suitable for use in raising broilers, which are hen chickens usually marketed around 10 weeks of age. However, it is believed to also be applicable to the raising of capons.

The feeding method of this invention may also reduce the cholesterol content of the meat in the finished chickens. This cholesterol reducing effect becomes more pronounced as the protein content of the diet is increased, being especially marked with diets containing more protein than normally required at the age of the chickens.

DETAILED DESCRIPTION

This invention is concenred with a method of producing chicken for meat production, including hens and capons. The invention is also concerned with feed compositions for use in the method. The method utilizes a feed additive which is not present in natural feeds, the keto-analog of leucine; namely, alphaketoisocaproate (KIC).

For the puposes of the present invention, the KIC should be in an edible nutritionally-absorbable form. For example, it may be used as its sodium, postassium, ammonium or calcium salt. Ammonium and alkali metal salts are more water-soluble, while alkaline earth metal salts such as calcium salt are less water-insoluble. For the purposes of this invention the more water-soluble KIC salts are preferred, such as sodium KIC.

Alpha-ketoisocaproate (KIC) is available commercially or can be synthesized by known procedures. KIC in the form of its sodium or calcium salts can be purchased from SOBAC, 336 Rue Saint-Honore, Paris, France, and/or through Sigma Chemical Company, St. Louis, Missouri. Sodium and calcium salts of KIC as supplied commercially are substantially pure compounds and are in the form of dry powders. However, high purity is not necessarily required for the purposes of the present invention.

KIC powders can be mixed with dry feeds for dry feed compositions or the water-soluble KIC salts can be administered by dissolving in drinking water. It is preferred to mix a dry KIC salt with the dry chicken feed ingredients at predetermined concentrations. The KIC salt can be incorporated by using standard mixing and blending equipment. KIC is probably substantially uniformly distributed throughout the feed. After mixing, if desired, the feed material may be further processed, such as by conversion to pellets.

The chicken feed compositions will usually be composed of mixtures of feed ingredients, including protein-providing ingredients. The feed compositions may comprise complete feeds or feed concentrates. The feeds preferably should contain at least a normally adequate amount of protein for the age of the chickens. Diets essentially deficient in protein should be avoided. Starter feeds containing at least 22% protein by weight (feed dry basis) are preferred for 0 to 4 weeks of age. Finishing rations used from 5 weeks on may contain a lesser amount of protein, but preferably contain at least 18% protein.

For optimized results, it is also believed desirable to include only limited quantities of proteinaceous feed ingredients which are high in leucine content. Such feed ingredients include blood meals, which may contain 16 to 20% leucine, and corn gluten meal containing 18 to 20% leucine (based on the protein dry weight). In contrast, soybean meal contains only about 8 to 9% leucine.

For the purpose of the present invention, it is preferred to limit the amount of leucine in the diet of the chickens to not over 12% by weight based on the dry weight of the total protein being conseumed. The amount of protein can be calculated by determining nitrogen and multiplying by a standard conversion factor of 6.25 (N×6.25). In preferred embodiments, the amount of leucine is limited to less than 10% by weight of total protein. Consequently, in the formulation of complete feeds or feed concentrates which are to provide a major portion of the diet of the chickens, it is desirable to maintain the leucine content of the feed composition at not over 12%. The preferred amount of leucine in the mixed feed is below 10% based on protein dry weight.

The method of this invention comprises orally administering to young chickens being raised for meat production at least 0.05 weight percent (wt %) of alpha-ketoisocaproate (KIC) based on the dry weight of the total feed diet. The amount of KIC can be referenced to sodium KIC and its molar equivalents. In preferred embodiments, the amount of KIC administered to the laying chickens is from 0.1 to 0.5 wt % KIC (sodium KIC basis) based on the dry weight of the feed consumed by the chickens. Higher levels of KIC, such as in the range from 0.5 to 1%, could be used but have not been found to provide any added benefit. The optimum range appears to be around 0.2 to 0.4% KIC.

For purposes of the present application, the specified weight amounts of KIC should be understood to be related to the sodium salt of KIC or a molar equivalent amount of the calcium salt or other salts or derivatives providing nutritionably absorbable and utilizable KIC.

When KIC is combined with the feed material as a uniform admixture, and the feed composition is intended to provide substantially the complete diet of the chickens, the amount of KIC may be specified in relation to the feed composition. For example, admixed feed compositions may contain from 0.05 to 1.0 wt % KIC (sodium KIC basis) in relation to the dry weight of the feed composition. In preferred embodiments for the formulation of complete feeds, the feed compositions preferably contain from 0.1 to 0.5 wt % KIC (sodium KIC basis) of the feed dry weight. The feed compositions also preferably contain at least an adequate amount of protein.

The chickens are preferably fed the KIC-containing diet from 0 to 6 weeks of age. The administration of KIC may be continued beyond 6 weeks, viz. up to 8 weeks of age, but the growth promotant benefits tend to lessen after 6 weeks, while tending to be maximized over the period from 0 to 4 weeks.

Illustrative feed compositions for use in practicing the present invention are set out below. The compositions are specially designed for use with chickens being raised for broiler production. Ration A is a 23% protein diet designed for use from 0 to 4 weeks of age, and Ration B is an 18% protein diet designed for use from 4 to 6, or from 4 to 8 weeks of age.

| RATION A (23% protein) | |
|---|---|
| Ingredients | Weight (lbs) |
| Ground Corn | 282.25 |
| Soybean Meal | 184.25 |
| Calcium Carbonate | 6.25 |
| Dicalcium Phosphate | 8.50 |
| Fat | 6.25 |
| Methionine Analog | 1.07 |
| Premix[1] | 11.43 |

| RATION B (18% protein) | |
|---|---|
| Ingredients | Weight (lbs) |
| Ground Corn | 350.75 |
| Soybean Meal | 119.50 |
| Calcium Carbonate | 9.75 |
| Dicalcium Phosphate | 7.50 |
| Premix[1] | 11.43 |

| Premix Composition[1] | |
|---|---|
| Vitamin A-30 | 234 grams |
| Vitamin D$_3$-40 | 54 grams |
| Vitamin K-16 | 63 grams |
| Vitamin E-125 | 36 grams |
| Riboflavin | 135 grams |
| Niacin | 63 grams |
| Calcium Panothanate | 27 grams |
| Choline | 1.33 lb. |
| Vitamin B$_{12}$ | 76.5 grams |
| Folic Acid | 4.5 grams |
| Nutrigard | 1.0 lb. |
| Methionine Analogue | 180 grams |
| Trace Minerals | 270 grams |
| Salt | 5 lbs. |
| Carrier | 35.5 lbs. |

Ration A contains a total of about 23% protein, of which approximately 9.8% is leucine. In Ration B, the percent protein is about 18, and the leucine 11% of the protein.

The method and feed compositions of this invention and the results obtainable thereby are further illustrated by the following examples.

EXAMPLE I

Feeding tests were conducted with the 23% Ration A and 18% Ration B diets set out above. Young hen chickens being raised for broiler production were used. The 18% protein diet contained less than the normal protein requirement, while the 23% protein diet contained adequate or slightly excess protein over normal requirements.

Sodium KIC was added to the 18% and 23% protein diets in amounts based on the dry weight of the diets comprising 0 (control), 0.03, .09 and 0.30%. Each test cell for receiving 18% or 23% protein diet at one level. After four weeks, the birds were transferred to floor pens (2 pens for each test group). In the continuing treatments from 5 to 8 weeks, each 2-pen group received one of the levels of the 18% or 23% protein diets.

The results are summarized below in Tables A and B.

The statistically significant results in Tables A and B have been starred. With the 18% protein diet, for weeks 0–4, KIC at 0.30% gave 73% growth improvement. With the 23% protein diet, 0.09% KIC gave 6% growth improvement, and 0.30 KIC gave 5% growth improvement for weeks 0–4. Over the whole period of the tests, the 0.09 and 0.30% KIC treatments, respectively, gave growth improvement of 4% and 6%.

EXAMPLE II

By mixing Ration A and B, a modified diet was prepared containing about 20% protein and approximately 10% leucine. This modified diet was compared with the 18% protein diet of Example I. The feeding period was 0 to 4 weeks of age, the KIC levels used were respectively 0 (control), 0.1, .2, and 0.4% based on the dry weight of the total feed rations. The birds were reared in four pens (30 birds per pen), four pens per treatment cell. At 4 weeks, the birds were all fed the 18% protein diet until slaughter. The results are summarized below in Tables C and D.

The results summarized in Tables C and D which were found statistically significant are starred. The 4-week growth data showed a positive response to KIC at 0.2 and 0.4% KIC levels. At both of these levels, improvement was obtained on the order of 4%, showing that KIC was acting as a growth promotant. The 22.5% protein diet was judged slightly deficient in protein for the normal requirements of the chickens from 0 to 4 weeks, while the 18% protein diet was deficient in protein for the period from 5 to 8 weeks.

EXAMPLE III

Additional tests were conducted using complete feed rations as illustrated in Example I, except that the protein contents were varied. In the first comparison, protein level was adjusted to 23% protein (10% leucine) and 27% protein (9% leucine). Sodium KIC was added to the compositions at levels of 0 (control), 0.05 and 0.15%. Each treatment cell consisted of six pens with 8 birds per pen. The results are summarized below in Table E.

In the second comparison, 16% protein (11% leucine) and 22% protein (10% leucine) feed rations were employed. Sodium KIC was added at 0 (control), 0.075 and 0.150%. Chickens which had been fed a normal diet without KIC from age 0 to 5 weeks were employed in a study of the effect of KIC in finishing rations for broilers from 6 to 9 weeks. The birds were used in floor pens with two pens per cell (30 birds/pen). The results are summarized below in Table F.

Test results of Table F show no significant changes in growth or carcass composition were noted. However, there was an apparent trend towards increase in fat pad weight with KIC in the 16% protein diet, which was considered to be deficient in protein. 22% protein diet was considered adequate.

TABLE A

| | 0-4 WEEKS (Battery Reared) | | |
|---|---|---|---|
| | % KIC | GAIN (g) | FEED/ GAIN |
| 18% protein | 0 | 797 | 1.63 |
| | .03 | 801 | 1.65 |
| | .09 | 780 | 1.65 |
| | .30 | 855* | 1.60 |
| 23 % protein | 0 | 824 | 1.52 |
| | .03 | 835 | 1.58 |
| | .09 | 874* | 1.52 |
| | .30 | 864* | 1.50* |

$p < .05$

TABLE B

| | 0-8 WEEKS (after 4 weeks pen-reared) | | | | | | |
|---|---|---|---|---|---|---|---|
| | % KIC in (2) DIET | GAIN (kg) | FEED/ GAIN | CARCASS (kg) | CARCASS (%) | % FAT (pad) | PROTEIN (% Carcass) | CHOLESTEROL (mg %) |
| 18% Protein | 0 | 2.46 | 2.10 | 1.76 | 71.0 | 1.94 | 19.4 | 145 |
| | .03 | 2.47 | 2.31 | 1.75 | 69.1 | 2.12 | 20.1 | 173 |
| | .09 | 2.43 | 2.23 | 1.43 | 69.4 | 1.88 | 20.0 | 119 |
| | .3 | 2.51 | 2.11 | 1.76 | 70.0 | 2.37 | 19.8 | 131 |
| 23% Protein | 0 | 2.49 | 2.21 | 1.83 | 70.2 | 1.83 | 20.12 | 159 |
| | .03 | 2.49 | 2.18 | 1.78 | 70.9 | 1.54 | 21.29* | 146 |
| | .09 | 2.60 | 2.17 | 1.86 | 70.1 | 1.61 | 20.90 | 82* |
| | .30 | 2.64* | 2.05* | 1.87 | 70.6 | 1.40 | 20.87 | 89* |

*$p < .05$

TABLE C

| 0-4 WEEKS (20.5% Protein) | | | |
|---|---|---|---|
| % KIC | PENS | GAIN (g) | FEED/ GAIN |
| 0 | 4 | 1017 | 1.53 |
| .1 | 4 | 1028 | 1.56 |
| .2 | 4 | 1062* | 1.54 |
| .4 | 4 | 1057* | 1.51 |

*$p < .05$

TABLE D

| 0-8 WEEKS (18% Protein > 4 weeks) | | | | | | |
|---|---|---|---|---|---|---|
| GAIN (Kg) | FEED/ GAIN | % CARC. | % FAT Pad | % PROTEIN | % FAT | CHOLESTEROL (mg %) |
| 2.24 | 1.94 | 76.2 | 2.94 | 22.67 | 17.09 | 161 |
| 2.27 | 2.01 | 77.0 | 2.85 | 23.05 | 16.27* | 180 |
| 2.28 | 1.95 | 75.8 | 3.09 | 23.18 | 16.73* | 171 |
| 2.25 | 1.90 | 76.6 | 2.92 | 23.08 | 16.50* | 168 |

*$p < .05$

TABLE E

| | PENS | % KIC | GAIN (g) | F/G | % BREAST FAT | MG % CHOLESTEROL |
|---|---|---|---|---|---|---|
| 23% Protein | 6 | 0 | 951 | 1.56 | 1.02 | 63 |
| | 6 | .05 | 962 | 1.57 | 1.01 | 63 |
| | 6 | .15 | 982* | 1.55 | 1.00 | 58 |
| 27% Protein | 6 | 0 | 973 | 1.54 | 1.07 | 58 |
| | 6 | .05 | 1028* | 1.50* | 1.00 | 56 |

TABLE E-continued

| PENS | % KIC | GAIN (g) | F/G | % BREAST FAT | MG % CHOLESTEROL |
|---|---|---|---|---|---|
| 6 | .15 | 1014* | 1.52 | 1.09 | 50 |

*p<.05.

TABLE F

| % KIC | | PEN | GAIN (Kg) | FEED/ GAIN | % CARC. | % PAD |
|---|---|---|---|---|---|---|
| 16% Protein | 0 | 2 | 1.32 | 3.52 | 64.7 | 2.08 |
| | .075 | 2 | 1.28 | 3.46 | 66.1 | 2.21 |
| | .150 | 2 | 1.18 | 3.44 | 66.6 | 2.38 |
| 22% Protein | 0 | 2 | 1.32 | 3.22 | 65.4 | 1.73 |
| | .075 | 2 | 1.29 | 3.29 | 66.0 | 2.10 |
| | .150 | 2 | 1.33 | 3.32 | 65.1 | 1.85 |

I claim:

1. The method of feeding chickens being raised for meat production to promote the growth of the chickens and to reduce the cholesterol content of the meat, comprising orally administering to said chickens an effective amount of alpha-ketoisocaproate (KIC) as a supplement to their feed diet during a substantial part of their growth period from 0 to 6 weeks of age, said diet containing sufficient leucine-containing protein for the normal requirements of said growing chickens, the amount of KIC administered corresponding to at least 0.05 weight percent (wt. %) of sodium KIC based on the dry weight of the total diet.

2. The method of claim 1 in which the amount of KIC administered corresponds to 0.05 to 0.5 wt. % sodium KIC based on the total feed diet.

3. The method of claims 1 or 2 in which said KIC is administered admixed with at least part of the feed diet.

4. The method of claims 1 or 2 in which said feed diet contains not over 12% leucine based on the dry weight of the total protein.

5. The method of feeding chickens being raised for meat production to promote the growth of the chickens and to reduce the cholesterol content of the meat, comprising admixing an effective amount of alpha-ketoisocaproate (KIC) with substantially complete feed rations for young chickens, said ration containing sufficient leucine-containing protein for the normal requirements of chickens 0 to 4 weeks of age but not over 12% leucine based on the dry weight of the total protein, the amount of KIC admixed corresponding to at least 0.05 weight percent (wt. %) sodium KIC based on the dry weight of the feed ration, and feeding said admixed ration to said chickens during their 0 to 4 weeks age growth period.

6. The method of claim 5 in which the amount of admixed KIC corresponds to 0.05 to 0.5 wt. % sodium KIC based on the dry weight of the feed ration.

7. The method of claims 5 or 6 in which said feed ration contains at least 22% protein based on the dry weight of the total protein and not over 10% leucine.

8. The method of claim 5 in which said chickens are hen chickens being raised for broiler production.

9. The method of claim 1 in which said ration contains at least 22% protein based on the dry weight of the feed ration, and not over 12% of said protein is leucine.

10. The method of claim 1 in which the amount of KIC administered corresponds to about 0.03 to 0.3 wt. % sodium KIC based on the total feed diet.

* * * * *